United States Patent [19]

Yamauchi et al.

[11] Patent Number: 4,738,782
[45] Date of Patent: Apr. 19, 1988

[54] METHOD AND APPARATUS FOR ASEPTIC FILTRATION

[75] Inventors: Hiroaki Yamauchi, Kakogawa; Takeshi Shiotani, Kobe; Yoshimitsu Mekata, Takasago; Satoshi Imai, Kobe, all of Japan

[73] Assignee: Kanegafuchi Kagaku Kogyo Kabushiki Kaisha, Osaka, Japan

[21] Appl. No.: 727,476

[22] Filed: Apr. 26, 1985

[30] Foreign Application Priority Data

Apr. 28, 1984 [JP] Japan .................................. 59-87603

[51] Int. Cl.$^4$ ......................... B10D 13/04; C12M 1/12
[52] U.S. Cl. ..................................... 210/650; 210/651; 210/500.36; 210/321.84; 435/311; 435/800; 528/488; 528/490; 528/493
[58] Field of Search .................. 210/500.2, 510.1, 927, 210/654, 650, 321.1, 645, 651, 500.21, 500.27, 500.33, 500.36, 500.37; 604/126, 190; 435/311, 800; 521/905; 528/487, 493, 490, 904, 488; 427/244, 245

[56] References Cited

U.S. PATENT DOCUMENTS

| | | | |
|---|---|---|---|
| 2,809,130 | 10/1957 | Rappaport | 156/310 |
| 3,425,991 | 2/1969 | Mortillaro et al. | 528/493 |
| 3,520,416 | 7/1970 | Keedwell | 604/126 |
| 3,948,823 | 4/1976 | Lee et al. | 210/500.2 |
| 3,993,625 | 11/1976 | Kurihara et al. | 210/500.33 |
| 4,032,440 | 6/1977 | Yasuda | 210/500.2 |
| 4,155,823 | 5/1979 | Gotcher et al. | 264/22 |
| 4,203,848 | 5/1980 | Grandine, II | 210/500.2 |
| 4,248,913 | 2/1981 | Jakabhazy et al. | 210/500.2 |
| 4,292,417 | 9/1981 | Ishii et al. | 210/500.33 |
| 4,302,336 | 11/1981 | Kawaguchi et al. | 210/500.33 |
| 4,340,482 | 7/1982 | Sternberg | 210/500.37 |
| 4,388,189 | 6/1983 | Kawaguchi et al. | 210/500.37 |
| 4,501,785 | 2/1985 | Nakanishi | 210/500.2 |
| 4,501,793 | 2/1985 | Sarada | 210/500.2 |
| 4,525,374 | 6/1985 | Vaillancourt | 604/190 |
| 4,557,955 | 12/1985 | Walch et al. | 210/927 |

FOREIGN PATENT DOCUMENTS

| | | | |
|---|---|---|---|
| 47569 | 4/1974 | Australia | 210/654 |
| 731610 | 4/1966 | Canada | 435/311 |
| 12557 | 6/1980 | European Pat. Off. | 210/500.2 |
| 80378 | 7/1978 | Japan | 210/500.2 |
| 69627 | 5/1980 | Japan | 210/500.2 |
| 6090838 | 7/1981 | Japan | 210/500.2 |
| 93734 | 6/1983 | Japan | 210/500.2 |
| 8003028 | 12/1981 | Netherlands | 210/500.2 |
| 84/04256 | 11/1984 | PCT Int'l Appl. | 210/650 |

OTHER PUBLICATIONS

Schonhorn and Hansen, "Surface Treatment of Polymers for Adhesive Bonding", *Journal of Applied Polymer Science*, vol. 11, pp. 1461–1474 (1967).

Schonhorn and Hansen, "Surface Treatment of Polymers", *Journal of Applied Polymer Science*, vol. 12, pp. 1231–1237 (1968).

Nelson et al, "Bonding of Teflon", *Industrial and Engineering Chemistry*, vol. 50, No. 3, Mar. 1958, pp. 329–330.

*Primary Examiner*—Richard V. Fisher
*Assistant Examiner*—Linda S. Evans
*Attorney, Agent, or Firm*—Armstrong, Nikaido, Marmelstein & Kubovcik

[57] ABSTRACT

A nutrient solution of a microorganism to be supplied to a fermentor or a culture broth in the fermentor is aseptically filtered by a porous filter medium made of polytetrafluoroethylene polymer and having properties impervious to microorganism, resistant to heat and chemicals, and hydrophilic, wherein said hydrophilic property was given to the surface of said filter medium with a treatment for hydrophilicity. This treatment comprises treating polytetrafluoroethylene porous polymer as a raw material for the filter medium with surface treating agent comprising an alkali metal naphthalene and diamine and immersing the treated polymer into concentrated sulfuric acid containing an aliphatic or aromatic aldehyde dissolved therein in a concentration exceeding half saturation.

14 Claims, 2 Drawing Sheets

METHOD AND APPARATUS FOR ASEPTIC FILTRATION

BACKGROUND OF THE INVENTION

1. Field of the Invention

This invention relates to a method and apparatus for quick and aseptic filtration of a nutrient solution during the supply of nutrient of a microorganism to a fermentor or a culture broth and during the collection of the supernatant of the broth from the fermentor. The term "supernatant" as used in this invention means the supernatant of culture broth.

2. Description of the Prior Art

As filter media heretofore used in supernatant collecting devices attached to or inserted into fermentors, or in medium feeding devices installed for supply of aqueous nutrient solution of microorganisms to fermentors, there are known (1) a filter medium formed of polyvinyl alcohol series hollow fibers, (2) a filter medium made of sintered metal, and (3) a filter medium formed of nitrocellulose series polymer membrane. The known media have defects when used. The polyvinyl alcohol series hollow fibers offer poor resistance to heat and undergo degradation at elevated temperatures and, therefore, do not withstand sterilization at temperatures exceeding 100° C. such as in an autoclave. The filter medium using the sintered metal is resistant to heat. When it is left standing in a culture broth for long time, however, the metal of the filter medium is dissolved by ionization and consequently causes detrimental transformation of the components of the culture medium and adversely affects the microorganism in the broth. Also the sintered metal itself undergoes degradation due to the ionization and fails to offer long service life. The nitrocellulose series polymer membrane, though excellent in heat resistance and durability, is deficient in membrane strength and porosity and, from the standpoint of membrane strength, is incapable of sampling a supernatant by vacuum suction with the aid of a syringe or pump.

SUMMARY OF THE INVENTION

This invention provides a method and apparatus for aseptic filtration of a nutrient solution of a microorganism to be supplied to a fermentor or a supernatant to be removed from the fermentor, by the use of a fluorine-containing polymer porous membrane showing high membrane strength, and which is excellent in resistance to heat and to chemicals, and in impeding the passage of microorganisms. The membrane surface is rendered hydrophilic through a treatment. It also provides a membrane material suitable for the aspectic filtration and devices used for the purpose of the aspectic filtration.

The other objects and characteristic features of the present invention will become apparent to those skilled in the art as the disclosure is made in the following description of a preferred embodiment of the invention, as illustrated in the accompanying drawings.

DESCRIPTION OF PREFERRED EMBODIMENTS OF THE INVENTION

Figure 1:
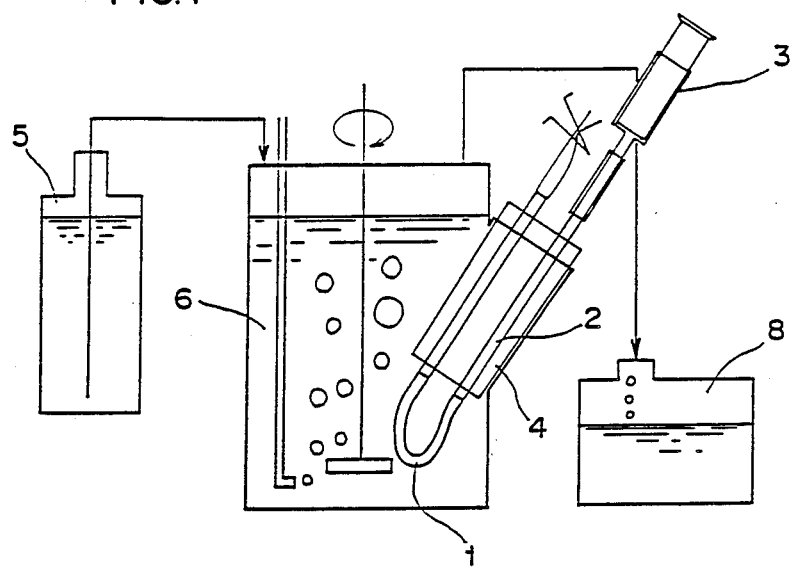
FIG. 1 and FIG. 2 are schematic diagrams illustrating culture systems provided with a supernatant collecting device (or nutrient supplying device) embodying the present invention.

The expression "porous polymer filter medium having the surface thereof rendered hydrophilic through a treatment" as used in this invention is meant to describe the filter medium as observed microscopically. By microscopic observation, the filter medium is found to be a porous article formed of intertwined filamentous or reticular fibers. The term "treatment" herein means rendering the surface of such filamentous or reticular fibers hydrophilic. The fluorine-containing polymer filter medium, with a surface which has been rendered hydrophilic through a specific treatment contemplated by this invention, acquires a membrane texture such that the cross section thereof is generally of a blackish to grayish color. Microscopically, when the membrane has its surface alone rendered hydrophilic by the aforementioned treatment, the central portion of the cross section of the membrane retains the white color inherent in the fluorine-containing polymer substance. In the case of the filter medium which has been given a treatment as just described, filtration by means of low pressure difference is found difficult because of the hydrophobicity of the central portion in the thickness of the membrane. Hereinafter, the fluorine-containing porous polymer filter medium whose surface has been microscopically rendered hydrophilic by the aforementioned specific treatment will be referred to simply as "hydrophilic porous polymer filter medium."

To be specific, this invention resides in a method for the aseptic filtration of a nutrient solution of a microorganism to be supplied to a fermentor, or a culture broth in the fermentor, which is characterized by effecting the aseptic filtration by the use of a hydrophilic porous polymer filter medium which is impervious to microorganisms and resistant to heat and chemicals. As the hydrophilic porous polymer filter medium which is impervious to microorganisms and resistant to heat and chemicals, to be used in this invention, a porous membrane or tube of a fluorine-containing polymer which has undergone the treatment for hydrophilicity is advantageously used.

Examples of the fluorine-containing polymer include polytetrafluoroethylene, polyhexafluoropropylene, trifluoroethylene, tetrafluoroethylene-hexafluoropropylene copolymer, and copolymers of fluorine-containing monomers with other hydrocarbon series monomers such as tetrafluoroethylene-propylene copolymer and tetrafluoroethylene-ethylene copolymer. The porous membrane formed from polytetrafluoroethylene, among the fluorine-containing polymers enumerated above, proves particularly desirable.

The treatment for rendering the surface of the porous fluorine-containing polymer membrane hydrophilic is carried out, for example, by the glow discharge method (CASING method) described as in Journal of Applied Polymer Science, 11, 1461–1474 (1967) and Journal of Applied Polymer Science, 12, 1231–1237 (1968) or any of the methods using alkali metals [such as the method using ammonia and an alkali metal as described in U.S. Pat. No. 2,809,130 and I.E.C., 50, (No. 3), pp. 329–330, March (1958), the method using a mixed solution of an alkali metal, naphthalene and tetrahydrofuran, the modified method using an organic alkali metal ("New Experimental Chemical Series," Vol. 12 "Organic Metal Chemistry," No. 43, 20, page 12, compiled by Japan Chemical Society, published by Maruzen Book Co., Ltd.), and the method using a mixed solution of an alkali metal, naphthalene, and diamine developed by the inventors]. All the methods described above impart hydrophilicity to the surface of the fluorine-containing polymer membrane by defluorinating the surface of the membrane.

The method using an alkali metal which has been developed by the inventors comprises immersing the fluorine-containing polymer membrane at 10° to 60° C. in a solution wherein an alkali metal such as sodium is added to a solution obtained by dissolving naphthalene in a diamine such as ethylene diamine or propylene diamine. Subsequently the wet membrane is treated in an atmosphere of dry inactive gas. In this case, the treatment produces a desirable effect when naphthalene is used in an amount of about 0.2 to 1 mol and the alkali metal in an amount of about 0.2 to 1 gram equivalent per liter of the diamine. The diamine may be used in the form of a mixed solution containing not less than 50% by volume of diamine in an ether such as tetrahydrofuran, dimethoxyethane, or ethylether, or a saturated hydrocarbon such as n-heptane or n-hexane, or benzene. The time of this treatment is in the range of one minute to 30 hours. Particularly the treatment continued for a duration of one to 30 minutes may be performed just once or repeated two to several times.

The porous fluorine-containing polymer membrane obtained by the aforementioned treatment for hydrophilicity can be used in its unmodified form as the filter medium for the collection of a supernatant or as the filter medium for the supply of a nutrient solution. The treated surface of this membrane, however, is not yet sufficiently resistant to alkali, acid, and heat. When this membrane is subjected to sterilization at elevated temperatures, particularly at temperatures exceeding 121° C., or to a treatment with a highly concentrated alkali, it does not always bring about a satisfactory result. When the membrane is intended for such a purpose as described above, the surface of the membrane rendered hydrophilic by defluorination is treated for stabilization with concentrated sulfuric acid having aldehyde dissolved therein. When the defluorinated surface is treated with the formalin/sulfuric acid mixture, the defluorinated carbons are cross-linked with the aldehyde to permit a notable improvement in resistance to chemicals and heat. The expression "cross-linking of aldehyde" as used in this invention embraces a case wherein an unsaturated bond between carbons is converted by the aldehyde into a saturated bond and further embraces a cross-linking occuring between adjacent carbon chains.

Examples of the aldehyde usable in the aforementioned mixed solution include formaldehyde, paraformaldehyde, acetaldehyde, propion aldehyde, glyoxal, succin dialdehyde, acrolein, croton aldehyde, propiol aldehyde, benzaldehyde, and terephthal aldehyde. Among the aldehydes enumerated above, paraformaldehyde proves particularly advantageous. The aldehyde dissolved in concentrated sulfuric acid in concentration of full saturation is used most advantageously. This solution is fairly effective so long as the concentration of the aldehyde exceeds half saturation. The reason is that the layer of the membrane rendered hydrophilic is inherently unstable to resist acids and, therefore, in proportion as the concentration of the aldehyde increases, the extent to which the stabilizing reaction of the aldehyde proceeds increases and the proportion of the decomposition by the acid decreases. The concentrated sulfuric acid is desired to have concentration of at least 90%. The result is particularly advantageous where the concentration of sulfuric acid is 98%. Actually in the case of paraformaldehyde, for example, since it is a solid substance, it may be added in an excess amount of sulfuric acid and held mixed therewith. As a result, paraformaldehyde is dissolved in sulfuric acid and acts as formaldehyde. The stabilizing reaction is desired to be carried out at a temperature in the range of 10° C. to 100° C., preferably 20° C. to 70° C. The reaction time, although variable with the reaction temperature, is proper in the range of 20 minutes to two days.

The membrane which has undergone the aforementioned treatment for hydrophilicity and the treatment for stabilization possesses hydrophilicity, excels in resistance to heat and chemicals, and retains the properties of the original fluorine-containing polymer membrane substantially intact. In other words, the membrane produced in consequence of the treatment for hydrophilicity and the treatment for stabilization, when used as a filter medium, is wettable with water, permits filtration of a large volume of an aqueous solution at low pressure, and retains its properties intact even after autoclaving 20 times (121° C. for 15 minutes). In 5N aqueous solutions of nitric acid, sulfuric acid, sodium hydroxide, and potassium hydroxide, for example, the filter medium remains intact for one week. The membrane possesses high enough strength to avoid fracture due to the influence of vacuum suction caused by a pump. Thus, the filter medium formed of this membrane permits safe sampling of the supernatant.

The pore diameter of the porous filter medium to be used for this invention can be freely selected to suit the purpose for which the filter medium is intended. For use during the supply of nutrient of a microorganism to a fermentor, the porous filter medium is required to have a pore diameter in the range of 0.05 $\mu$m to 10 $\mu$m in due consideration of normal sizes of microorganisms (bacteria, yeasts, fungi, etc.). For thorough removal by filtration of contaminants (including spores) present in nutrients, the filter medium is desired to have a pore diameter in the range of 0.05 $\mu$m to 0.1 $\mu$m. In this respect, the pore diameter of the filter medium is generally determined by the bubbling method.

For the purpose of aseptic collection of the supernatant, the filter medium is required to have a pore diameter in the range of 0.05 $\mu$m to 10 $\mu$m in consideration of sizes of microorganisms present within the fermentor. For thorough removal of still smaller microorganisms such as bacteria, it is proper for the filter medium to have a pore diameter in the range of 0.05 $\mu$m to 3 $\mu$m. In any event, the pore diameter to be selected is required to be small enough to stop the passage of the microorganisms in the fermentor which are desired to be removed by filtration.

Figure 2:
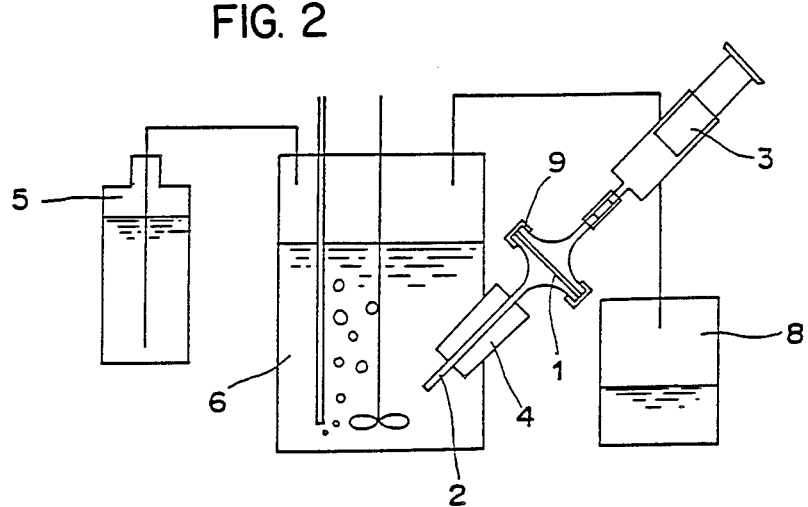
Figure 3:
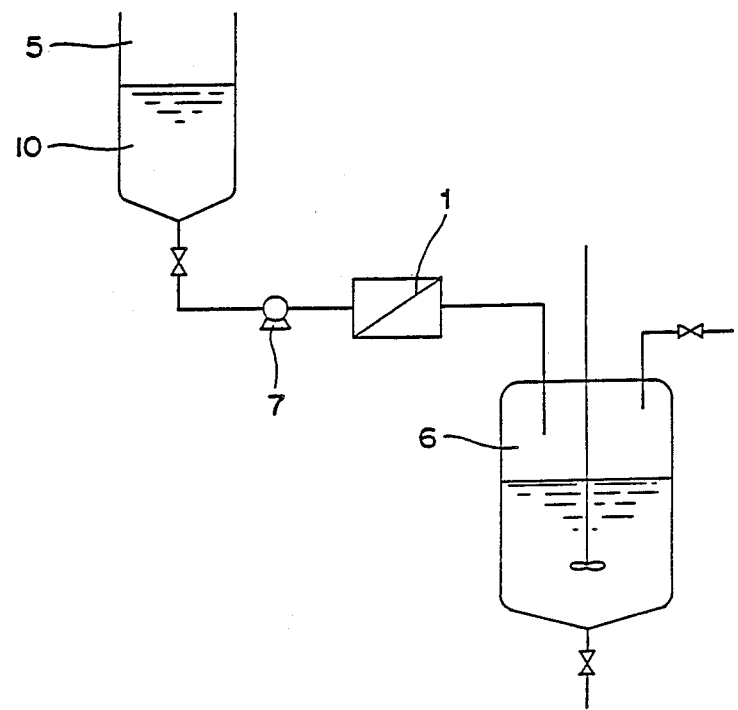
FIG. 3 is a schematic diagram illustrating a nutrient supplying device embodying the present invention.

Aseptic supply of nutrient of a microorganism on the laboratory scale, for example, can be effected by placing an aqueous solution of such nutrient in a nutrient supplying device comprising a glass tube (2) provided with a filter medium (1) of the form of a tube or film as illustrated in FIG. 1 or FIG. 2, and a syringe (3) connected to one end of the glass tube and extruding the aqueous solution out of the device. A silicone rubber plug (4) may be used to hold the glass tube (2) in place. A waste liquid tank (8) may also be provided. A clamp (9) may be added between the glass tube (1) and the syringe (3). On the commercial plant scale, the aseptic supply can be effected by interposing a pump (7) and a filter medium (1) between a nutrient supply tank (5) and a fermentor (6) as illustrated in FIG. 3, and causing an aqueous nutrient solution (10) to be pumped into the fermentor. In this case, the filter medium may be in the form of a flat membrane, hollow-fiber membrane, or a tubular ultrafiltration membrane. The nutrient supplying device described above is also embraced by the present invention.

The use of the method of this invention for the aseptic collection of the supernatant can be effected by the use of a supernatant collecting device which comprises a glass tube, a filter medium (1) in the form of a tube connected to one end of the glass tube, a glass tube (2) connected to the other end of the tubular filter medium, and a syringe (3) detachably connected through the medium of the glass tube (2) to the tubular filter medium as illustrated in FIG. 1. Also, a collector which comprises a filter medium (1) in the form of a film and a flared glass tube tightly enclosing the filter medium therein as illustrated in FIG. 2 can be used. In this case, the suction caused by the syringe enables the supernatant to be sampled aseptically. Of course, on the commercial plant scale, the aseptic collection of the supernatant may be carried out more efficiently by enhancing the force of solution with a vacuum pump in the place of the syringe, or increasing the inner pressure of the vessel. The glass tubes aforementioned may be replaced with metallic or plastics tubes. The device described above is also embraced in the technical scope of the present invention.

Unlike the conventional filter medium which has suffered some critical defect or other for the purpose of application to the fermentation industry, the method of aseptic filtration contemplated by the present invention is free from such drawbacks and exhibits outstanding properties and promises ample feasibility in the fermentation industry. Particularly, the fluorine-containing polymer filter medium whose surface is rendered hydrophilic in advance and has been further stabilized by the treatment with the formalin/sulfuric acid mixture offers ample resistance to the impact of autoclaving treatment performed at 121° C. for 15 minutes as generally performed for the purpose of sterilization. The medium also excels in durability to resist chemicals. As a feature shared commonly by all fluorine-containing polymer membranes, the filter medium of this invention enjoys the advantage that, unlike a filter medium made of sintered metal, the filter medium is not susceptible to degradation by ionization. Further, this filter medium has strength which is high enough for the membrane to be manufactured in high porosity (on the order of 60 to 80% as compared with the level of not more than 50% the conventional filter medium has been able to possess). Owing to the higher porosity, the filter medium of this invention enjoys a notable increase in speed of filtration.

Now, the present invention will be described more specifically below with reference to working examples. It should be noted that this invention is not limited in any respect to or by these examples.

EXAMPLE 1

In a test tube having an inner volume of 100 ml and provided with a ground stopper, 75 ml of ethylene diamine and 7 g of naphthalene were placed and allowed to dissolve into each other and, then, 2 g of metallic sodium cut in strips (about 1 mm × 1 mm × 20 mm) was thrown in the resultant solution. Then, the test tube was tightly closed with the stopper. The test tube was sealed in a bag of polyethylene filled with dry nitrogen gas and was shaken thoroughly to induce a reaction of the sodium with the naphthalene. When the reaction temperature reached 45° C., a porous tube of polytetrafluoroethylene (a product of Sumitomo Electric Industries, Ltd. having an inside diameter of 3 mm, an outside diameter of 4 mm, porosity of 60%, and pore diameter of 0.1 μm, and marketed under trademark designation of "Poreflon") cut in a length of 10 cm was thrown into the aforementioned test tube and left standing therein at 45° C. for about two minutes to be reacted by the solution. The treated tube was treated with methanol to inactivate the sodium acting on the tube, washed with tetrahydrofuran, and washed further with cold water. The tube consequently obtained was dried in a draft for three hours. It was immersed in 30 ml of a mixed solution of concentrated sulfuric acid having 10 g of paraformaldehyde added thereto and then left standing therein at room temperature for 24 hours. The tube was removed from the mixed solution, washed with cold water, washed further with tetrahydrofuran, and dried in a draft.

To one end of the resultant polytetrafluoroethylene tube having a hydrophilic surface, a glass tube fitted with a silicone tube having the free end thereof sealed with a pinch cock was connected. To the other end thereof, a syringe was connected through the medium of a glass tube and a silicone tube. Consequently, there was completed a supernatant collecting device. This device was secured on a fermentor with a silicone stopper and, with 2 liters of culture medium placed therein, sterilized by autoclaving at 121° C. for 15 minutes. The culture medium had a composition shown in Table 1.

TABLE 1

| Composition of culture medium | Concentration (ppm) |
| --- | --- |
| 75% $H_3PO_4$ | 2,500 |
| KCl | 2,000 |
| $MgSO_4(7H_2O)$ | 2,000 |
| Ammonium sulfate | 500 |
| NaCl | 100 |
| $CaCl_2(2H_2O)$ | 100 |
| $FeSO_4(7H_2O)$ | 100 |
| $ZnSO_4(7H_2O)$ | 100 |
| $MnSO_4$(4 to $6H_2O$) | 20 |
| $CuSO_4(5H_2O)$ | 5 |
| Biotin | 0.1 |
| Vitamin $B_1$ | 20 |
| Vitamin $B_6$ | 1 |
| Calcium pantothenate | 20 |
| Inositol | 100 |
| Nicotinic acid | 1 |
| Folic acid | 0.01 |
| Glucose | 10,000 |
| Yeast extract | 1,000 |

Thereafter, 5 g of wet cells of baker's yeast, *Saccharomyces cerevisiae*, was aseptically inoculated to 2 liters of culture medium in a fermentor and was cultivated in continuous culture for one week under the conditions of pH 4.7, DO 2 to 3 ppm, temperature 31° C., and dilution rate 0.2 (liter/hour). The supernatant was sampled at an interval of about one hour. For a short period of one or two seconds, the supernatant could be collected in a sample size of 1 to 2 ml with ease. During the continuous culture for one week, the supernatant could be collected quickly without the tubular filter medium experiencing any clogging and consequent adverse effects. Microscopic observation of the collected supernatant confirmed perfect absence of yeast. When 1 ml of the sampled supernatant was inoculated inside a sterile cup-board to a culture medium of the composition of Table 1 plus 2% of agar and incubated at 30° C. for three days, on the culture medium, no colony of yeast appeared.

EXAMPLE 2

By following the procedure of Example 1, the same culture medium was placed in the fermentor after subsequent sterilization, 5 g of wet cells of *Saccharomyces cerevisiae* was aseptically inoculated to the fermentor. The microorganism was cultured in continuous culture for one week by feeding an aqueous solution of vitamin containing biotin and inositol to the fermentor, with the nutrient supplying device at interval of one hour. The supply of the aqueous solution of vitamin in a volume of 10 to 20 ml could be completed in a matter of one to two seconds. After the continuous culture for one week, the tubular filter medium was not found to suffer from clogging and attendant adverse effects. Under a microscope, the broth showed absolutely no sign of contamination with any contaminant in the continuous culture for one week.

EXAMPLE 3

Solutions, several containing $10^7$ microorganisms of baker's yeast, *Escherichia coli*, and *Bacillus subtilis* were prepared. The supernatants of the solutions were collected with the same collecting device as used in Example 1. A 1-ml portion of the supernatant so collected was inoculated within a sterile cup-board to a culture medium of the composition of Table 1 plus 2% of agar and incubated at 30° C. for three days. No microorganic colony appeared on the culture medium. This fact shows that the collector provided with the tubular filter medium effected removal of the microorganisms.

EXAMPLE 4

The same collecting device as used in Example 1 was subjected to a total of 20 times of autoclaving (121° C. for 15 minutes) and then put to use in the same continuous culture as in Example 1. The results in terms of amount of sample collected, clogging of tubular filter medium, and effect in removal of microorganisms were the same as those of Example 1. This fact represents that the tubular filter medium possesses outstanding stability to resist heat.

EXAMPLE 5

The same collecting device as used in Example 1 was left standing for ten hours each in 5N sulfuric acid and 5N sodium hydroxide solutions. Then, it was put to use in the same culture as in Example 1. The results in terms of speed of collection, clogging of tubular filter medium, and effect of removal of microorganisms were the same as those of Example 1. This fact shows that the tubular filter medium possesses outstanding stability to withstand chemicals.

EXAMPLE 6

Continuous culture was carried out by following the procedure of Example 1, except that *Escherichia coli* was used in the place of baker's yeast. The results were entirely the same as those obtained by using baker's yeast. The supernatant consequently formed was collected by the use of the same collecting device as used in Example 1 and aseptically inoculated inside a sterile cup-board to the culture medium of the composition of Table 1 plus 2% of agar, and incubated at 30° C. for three days. No microorganic colony appeared on the medium.

EXAMPLE 7

Continuous culture was carried out by following the procedure of Example 1, except that the device of FIG. 2 was used in the place of the supernatant collecting device of FIG. 1. The supernatant was sampled at intervals of about one hour. The collection of the supernatant in a volume of 1 to 2 ml could be completed in a matter of one to two seconds. During the continuous culture for one week, the supernatant collection could be made quickly without the filter medium experiencing any clogging. Under a microscope, the supernatant showed absolutely no yeast. When 1 ml of the collected supernatant was inoculated inside a sterile cup-board to a medium of the composition of Table 1 plus 2% of agar and incubated at 30° C. for three days, no colony of yeast appeared on the medium.

What is claimed is:

1. A method for aseptic filtration of a nutrient solution wherein nutrient of a microorganism is aseptically filtered during the supply of nutrient to a fermentor or a culture broth is aseptically filtered during the collection of supernatant of the culture broth from the fermentor, said method comprising:
   (a) passing a solution to be filtered through a porous filter medium made of a polytetrafluoroethylene polymer, said filter medium being impervious to microorganisms, resistant to heat and chemicals, and having a hydrophilic property which was given to the surface of said filter medium by treating said filter medium to achieve hydrophilicity by the steps of
      (i) contacting a polytetrafluoroethylene porous polymer with a surface treating agent which will impart hydrophilicity, said surface treating agent comprising an alkali metal, naphthalene and diamine, and
      (ii) immersing said polymer in a concentrated sulfuric acid containing an aliphatic or aromatic aldehyde dissolved therein in a concentration exceeding half saturation to stabilize the filter medium; and,
   (b) obtaining a resulting filtrate.

2. The method of claim 1, wherein said filter medium is in the form of a tube or a film.

3. The method of claim 1, wherein nutrients of a microorganism are supplied into a fermentor by the use of a porous filter medium containing pores 0.05 μm to 10 μm in diameter.

4. The method of claim 1 wherein the pores of the porous filter medium have a pore diameter which falls in the range of 0.05 um to 0.1 um.

5. The method of claim 1, wherein a culture broth is collected from a fermentor by the use of a porous filter medium containing pores 0.05 μm to 10 μm in diameter.

6. The method of claim 1 wherein the pores of the porous filter medium have a pore diameter which falls in the range of 0.05 um to 3 um.

7. A device for the aseptic collection of a supernatant of a culture broth comprising a collector which is provided therein with a porous filter medium made of a polytetrafluoroethylene polymer, said filter medium being pervious to said supernatant, impervious to microorganisms, resistant to heat and chemicals, and provided with a hydrophilic property which was given to the surface of said filter medium by treating said filter medium to achieve hydrophilicity by the steps of (i) contacting a polytetrafluoroethylene porous polymer with a surface treating agent which will impart hydrophilicity, said surface treating agent comprising an alkali metal, naphthalene and diamine, and (ii) immersing said polymer in a concentrated sulfuric acid containing an aliphatic or aromatic aldehyde dissolved therein in a concentration exceeding half saturation to stabilize the filter medium.

8. The device of claim 7, wherein said filter medium is in the form of a tube or a flat membrane.

9. The device of claim 7, wherein said filter medium contain pores 0.05 μm to 10 μm in diameter.

10. The device of claim 7, wherein said filter medium contains pores of 0.05 um to 3 um in diameter.

11. A device for the aseptic supply of a culture medium to a fermentor, said device comprising a passage means for the culture medium, wherein said passage means is provided therein with a porous filter medium made of a polytetrafluoroethylene polymer, said filter medium being pervious to water and nutrient of a microorganism, impervious to microorganisms, resistant to heat and chemicals, and having a hydrophilic property which was given to the surface of said filter medium by treating said filter medium to achieve hydrophilicity by the steps of (i) contacting a polytetrafluoroethylene porous polymer with a surface treating agent which will impart hydrophilicity, said surface treating agent comprising an alkali metal, naphthalene and diamine, and (ii) immersing said polymer in a concentrated sulfuric acid containing an aliphatic or aromatic aldehyde dissolved therein in a concentration exceeding half saturation to stabilize the filter medium.

12. The device of claim 11, wherein said filter medium is in the form of a tube or a flat membrane.

13. The device of claim 11, wherein said filter medium contains pores 0.05 μm to 10 μm in diameter.

14. The device of claim 11, wherein said filter medium contains pores of 0.05 um to 0.01 um in diameter.

* * * * *